(12) United States Patent
Finn et al.

(10) Patent No.: US 7,642,055 B2
(45) Date of Patent: *Jan. 5, 2010

(54) TWO-COLOR REAL-TIME/END-POINT QUANTITATION OF MICRORNAS (MIRNAS)

(75) Inventors: Andrew K. Finn, San Francisco, CA (US); Caifu Chen, Palo Alto, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 247 days.

This patent is subject to a terminal disclaimer.

(21) Appl. No.: 11/232,475

(22) Filed: Sep. 21, 2005

(65) Prior Publication Data

US 2006/0078924 A1  Apr. 13, 2006

Related U.S. Application Data

(60) Provisional application No. 60/612,199, filed on Sep. 21, 2004.

(51) Int. Cl.
*C12P 19/34* (2006.01)
*C07H 21/04* (2006.01)

(52) U.S. Cl. .................... 435/6; 536/24.2; 536/24.3

(58) Field of Classification Search ........................ None
See application file for complete search history.

(56) References Cited

U.S. PATENT DOCUMENTS

| | | | |
|---|---|---|---|
| 4,683,202 A | | 7/1987 | Mullis |
| 4,800,159 A | | 1/1989 | Mullis et al. |
| 5,210,015 A | * | 5/1993 | Gelfand et al. ........... 435/6 |
| 5,538,848 A | | 7/1996 | Livak et al. |
| 5,874,260 A | * | 2/1999 | Cleuziat et al. ........... 435/91.2 |
| 5,876,927 A | | 3/1999 | Lebo et al. |
| 5,876,930 A | | 3/1999 | Livak et al. |
| 5,882,864 A | | 3/1999 | An et al. |
| 5,952,202 A | | 9/1999 | Aoyagi et al. |
| 6,030,787 A | | 2/2000 | Livak et al. |

(Continued)

FOREIGN PATENT DOCUMENTS

WO   WO 00/79009 A2   12/2000

(Continued)

OTHER PUBLICATIONS

Brennecke et al. Towards a complete description of the microRNA complement of animal genomes. Genome Biology 2003, vol. 4, pp. 228.1-228.3.*

(Continued)

*Primary Examiner*—Young J Kim
*Assistant Examiner*—Samuel Woolwine

(57) ABSTRACT

The present invention is directed to methods, reagents, kits, and compositions for detecting target polynucleotide sequences, especially small target polynucleotides such as miRNAs, between two samples. A pair of linker probes can be employed in two different reactions to query a particular species of target polynucleotide. A pair of detector probes, a single forward primer specific for the target polynucleotide, and a reverse primer can be employed in an amplification reaction to query the difference in expression level of the target polynucleotide between the two samples. In some embodiments a plurality of small miRNAs are queried with a plurality of linker probes. The plurality of queried miRNAs can then be decoded in a plurality of amplification reactions.

14 Claims, 3 Drawing Sheets

U.S. PATENT DOCUMENTS

| | | | |
|---|---|---|---|
| 6,037,130 A * | 3/2000 | Tyagi et al. | 435/6 |
| 6,040,166 A | 3/2000 | Erlich et al. | |
| 6,090,557 A | 7/2000 | Weiss | |
| 6,114,152 A | 9/2000 | Serafini et al. | |
| 6,117,635 A | 9/2000 | Nazarenko et al. | |
| 6,197,563 B1 | 3/2001 | Erlich et al. | |
| 6,258,569 B1 | 7/2001 | Livak et al. | |
| 6,270,967 B1 | 8/2001 | Whitcombe et al. | |
| 6,358,679 B1 | 3/2002 | Heid et al. | |
| 6,403,319 B1 | 6/2002 | Lizardi et al. | |
| 6,498,025 B1 | 12/2002 | Miller | |
| 6,582,936 B1 | 6/2003 | Serafini et al. | |
| 6,605,451 B1 | 8/2003 | Marmaro et al. | |
| 6,692,915 B1 | 2/2004 | Nallur | |
| 6,764,821 B1 | 7/2004 | Rabbani et al. | |
| 6,777,180 B1 * | 8/2004 | Fisher et al. | 435/6 |
| 6,821,727 B1 | 11/2004 | Livak et al. | |
| 6,884,583 B2 | 4/2005 | Livak et al. | |
| 2003/0235854 A1 | 12/2003 | Chan et al. | |
| 2004/0175732 A1 | 9/2004 | Rana | |
| 2004/0214196 A1 | 10/2004 | Aydin | |
| 2005/0059049 A1 | 3/2005 | Moen et al. | |
| 2005/0260640 A1 | 11/2005 | Andersen et al. | |
| 2005/0266418 A1 | 12/2005 | Chen et al. | |
| 2005/0272071 A1 | 12/2005 | Lao et al. | |
| 2006/0035215 A9 * | 2/2006 | Sorge et al. | 435/6 |
| 2006/0035217 A1 | 2/2006 | Livak et al. | |
| 2006/0057595 A1 | 3/2006 | Lao et al. | |
| 2006/0063163 A1 | 3/2006 | Chen et al. | |
| 2006/0078924 A1 | 4/2006 | Finn et al. | |
| 2006/0194225 A1 | 8/2006 | Spier | |
| 2007/0015176 A1 | 1/2007 | Lao et al. | |
| 2007/0048757 A1 | 3/2007 | Lao et al. | |
| 2007/0111226 A1 | 5/2007 | Tan et al. | |

FOREIGN PATENT DOCUMENTS

| | | | |
|---|---|---|---|
| WO | WO 02/061143 A2 | | 8/2002 |
| WO | WO 02061143 A2 | * | 8/2002 |
| WO | WO 2004022784 A2 | * | 3/2004 |

OTHER PUBLICATIONS

U.S. Appl. No. 10/944,153, filed Sep. 16, 2004.
U.S. Appl. No. 60/711,480, filed Aug. 24, 2005.
U.S. Appl. No. 60/750,302, filed Dec. 13, 2005.
C. Chen et al., "Real-time PCR: Advancing RNA Interference and MicroRNA Studies" Pharmaceutical Discovery Online, May 1, 2005, pp. 1-5.
J. Guegler et al., "Quantitation of Plant miRNAs by RT-PCR" 2004, publication from Applied Biosystems website, URL: http://docs.appliedbiosystems.com, retrieved on Feb. 2, 2006, 1 page.
International Search Report and Written Opinion mailed Feb. 21, 2006 issued in International Application No. PCT/US2005/033943, 14 pages.
File History of U.S. Appl. No. 10/947,460, filed Sep. 21, 2004.
File History of U.S. Appl. No. 11/142,720, filed May 31, 2005.
Lane et al., The Thermodynamic Advantage of DNA Oligonucleotide 'Stacking Hybridization' Reactions: Energetics of a DNA Nick, Nucleic Acids Research 25(3):611-616 (1997).
Stratagene Catalog 1988 (cover and p. 39).

* cited by examiner

TWO-COLOR REAL-TIME/END-POINT QUANTITATION OF MICRORNAS (MIRNAS)

RELATED APPLICATIONS

This application claims a benefit under 35 U.S.C. §119(e) from U.S. Application No. 60/612,199, filed Sep. 21, 2004, which is incorporated herein by reference.

FIELD

The present teachings are in the field of molecular and cell biology, specifically in the field of detecting target polynucleotides such as miRNA.

INTRODUCTION

RNA interference (RNAi) is a highly coordinated, sequence-specific mechanism involved in posttranscriptional gene regulation. During the initial steps of process, a ribonuclease (RNase) II-like enzyme called Dicer reduces long double-strand RNA (dsRNA) and complex hairpin precursors into: 1) small interfering RNAs (siRNA) that degrade messenger RNA (mRNA) and 2) micro RNAs (miRNAs) that can target mRNAs for cleavage or attenuate translation.

The siRNA class of molecules is thought to be comprised of 21-23 nucleotide (nt) depluxes with characteristic dinucleotide 3' overhangs (Ambros et al., 2003, RNA, 9 (3), 277-279). siRNA has been shown to act as the functional intermediate in RNAi, specifically directing cleavage of complementary mRNA targets in a process that is commonly regarded to be an antiviral cellular defense mechanism (Elbashir et al., 2001, Nature, 411:6836), 494-498, Elbashir et al., 2001, Genes and Development, 15 (2), 188-200). Target RNA cleavage is catalyzed by the RNA-induced silencing complex (RISC), which functions as a siRNA directed endonuclease (reviewed in Bartel, 2004, Cell, 116 (2), 281-297).

Micro RNAs (miRNAs) typically comprise single-stranded, endogenous oligoribonucleotides of roughly 22 (18-25) bases in length that are processed from larger stem-looped precursor RNAs. The first genes recognized to encode miRNAs, lin-4 and let-7 of C. elegans, were identified on the basis of the developmental timing defects associated with the loss-of-function mutations (Lee et al., 1993, Cell, 75 (5), 843-854; Reinhart et al., 2000, Nature, 403, (6772), 901-906; reviewed by Pasquinelli et al., 2002, Annual Review of Cell and Developmental Biology, 18, 495-513). The breadth and importance of miRNA-directed gene regulation are coming into focus as more miRNAs and regulatory targets and functions are discovered. To date, a total of at least 700 miRNAs have been identified in C. elegans, Drosophila (Fire et al., 1998, Nature, 391 (6669(805-811), mouse, human (Lagos-Quintana et al., 2001, Science, 294 (5543), 853-858), and plants (Reinhart et al., 2002, Genes and Development, 16 (13), 1616-1626). Their sequences are typically conserved among different species. Size ranges from 18 to 25 nucleotides for miRNAs are the most commonly observed to date.

The function of most miRNAs is not known. Recently discovered miRNA functions include control of cell proliferation, cell death, and fat metabolism in flies (Brennecke et al., 2003, cell, 113 (1), 25-36; Xu et al, 2003, Current Biology, 13 (9), 790-795), neuronal patterning in nematodes (Johnston and Hobert, 2003, Nature, 426 (6968), 845-849), modulation of hematopoietic lineage differentiation in mammals (Chen et al., 2004, Science, 303 (5654), 83-87), and control of leaf and flower development in plants (Aukerman and Sakai, 2003, Plant Cell, 15 (11), 2730-2741; Chen, 2003, Science, 303 (5666):2022-2025; Emery et al., 2003, Current Biology, 13 (20), 1768-1774; Palatnik et al., 2003, Nature, 425 (6955), 257-263). There is speculation that miRNAs may represent a new aspect of gene regulation.

Most miRNAs have been discovered by cloning. While there are a few cloning kits available for researchers from Ambion and QIAGEN, the process is laborious and not very accurate. Further, there has been little reliable technology available for miRNA quantitation (Allawi et al., Third Wave Technologies, RNA. 2004 July; 10(7):1153-61). Northern blotting has been used but results are not quantitative (Lagos-Quitana et al., 2001, Science, 294 (5543), 853-854). Many miRNA researchers are interested in monitoring the level of the miRNAs at different tissues, at the different stages of development, or after treatment with various chemical agents. However, the short length of miRNAs has made their study difficult.

SUMMARY

The present teachings provide a method for quantifying a small target polyncucleotide in each of two samples comprising; providing a first reaction mixture comprising a small target polynucleotide from a first sample, and a first linker probe, wherein the first linker probe comprises a 3' target-specific portion a, a stem, and a loop, wherein the 3' target-specific portion base pairs with the 3' end of the target polynucleotide; providing a second reaction mixture comprising a small target polynucleotide from a second sample, and a second linker probe, wherein the second linker probe comprises a 3' target-specific portion, a stem, and a loop, wherein the 3' target-specific portion base pairs with the 3' end of the target polynucleotide, wherein the small target polynucleotide in the first reaction mixture is the same species as the small target polynucleotide in the second reaction mixture; hybridizing the first linker probe to the small target polynucleotide in the first reaction mixture to form a first target-linker probe complex and hybridizing the second linker probe to the small target polynucleotide in the second reaction mixture to form a second target-linker probe complex; combining the first target-linker probe complex and the second target-linker probe complex to form a pooled reaction mixture, wherein the pooled reaction mixture comprises a first extension reaction product and a second extension reaction product; amplifying the first extension reaction product and the second extension reaction product in the presence of a first detector probe and a second detector probe to form an amplified first extension reaction product and an amplified second extension reaction product, wherein the first detector probe corresponds to the amplified first extension reaction product and the second detector probe corresponds to the second amplified second extension reaction product; and, detecting the quantity of the small target polynucleotide in the two samples by comparing the first detector probe and the second detector probe.

In some embodiments, the present teachings provide a kit comprising; a reaction vessel comprising a first linker probe; a reaction vessel comprising a second linker probe; wherein the first linker probe and the second linker probe comprise the same 3' target specific portion and different sample identifying portions.

In some embodiments, the present teachings provide a reaction mixture comprising; a first linker probe hybridized to a first species of a small target polynucleotide, and a second linker probe hybridized to a second species of the small target polynucleotide, wherein the first linker probe comprises a first sample identifying portion and the second linker probe comprises a second sample identifying portion.

BRIEF DESCRIPTION OF THE DRAWINGS

The skilled artisan will understand that the drawings, described below, are for illustration purposes only. The drawings are not intended to limit the scope of the present teachings in any way.

DESCRIPTION OF EXEMPLARY EMBODIMENTS

Figure 1:
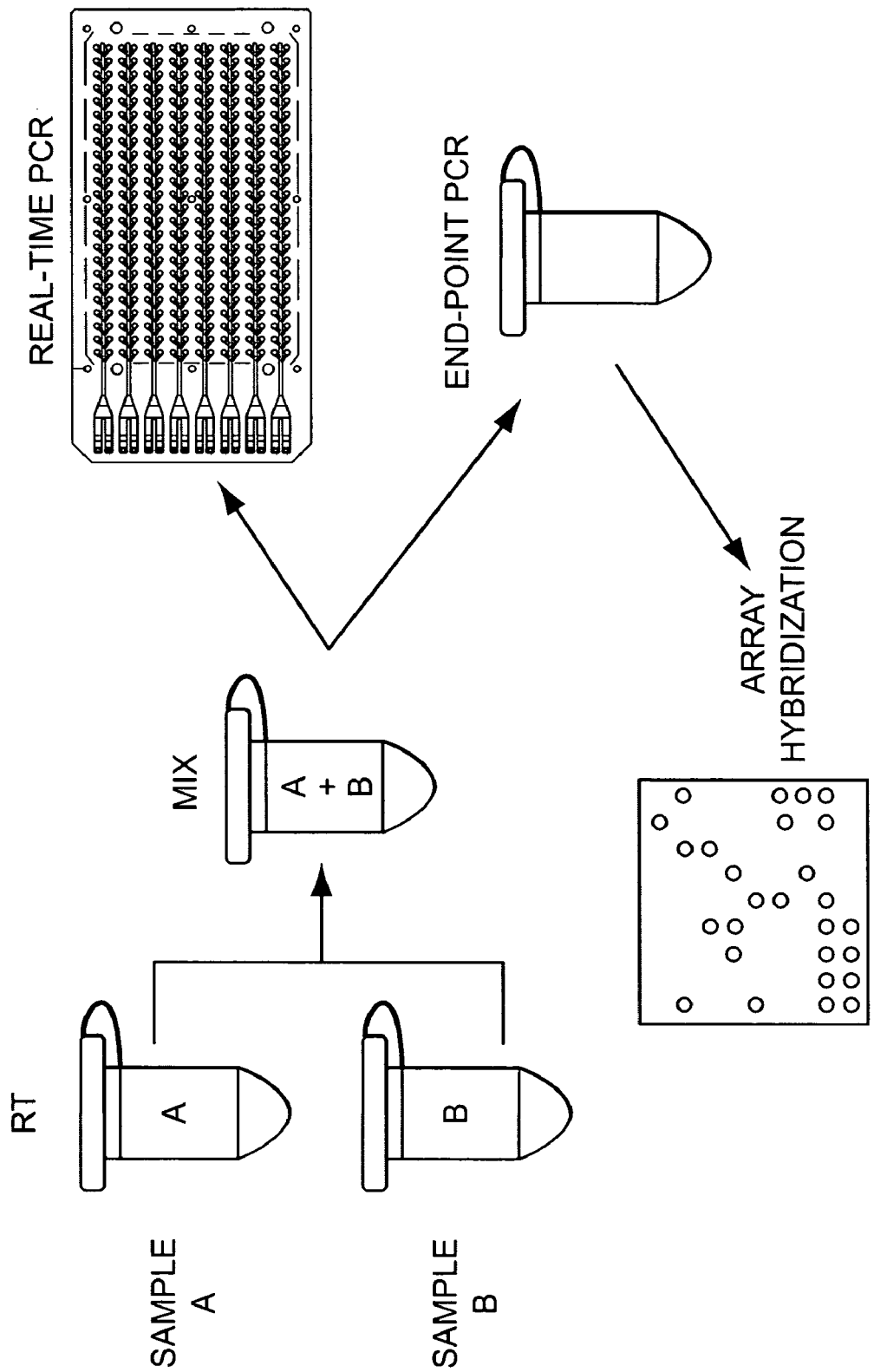
FIG. 1 depicts an overview according to some embodiments of the present teachings.

Aspects of the present teachings may be further understood in light of the following examples, which should not be construed as limiting the scope of the present teachings in any way. The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc discussed in the present teachings, such that slight and insubstantial deviations are within the scope of the present teachings herein. In this application, the use of the singular includes the plural unless specifically stated otherwise. For example, "a linker probe" means that more than one linker probe can be present; for example but without limitation, one or more copies of a particular linker probe species, as well as one or more versions of a particular linker probe type, for example but not limited to, a multiplicity of different first linker probes querying a multiplicity of different target polynucleotide species in a first sample. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the invention.

Some Definitions

As used herein, the term "target polynucleotide" refers to a polynucleotide sequence that is sought to be detected. The target polynucleotide can be obtained from any source, and can comprise any number of different compositional components. For example, the target can be nucleic acid (e.g. DNA or RNA), transfer RNA, siRNA, and any of a variety of small non-coding RNAs (see for example Science, 309:1567-1569 (2005)), and can comprise nucleic acid analogs or other nucleic acid mimics. The target can be methylated, non-methylated, or both. The target can be bisulfite-treated and non-methylated cytosines converted to uracil. Further, it will be appreciated that "target polynucleotide" can refer to the target polynucleotide itself, as well as surrogates thereof, for example amplification products, and native sequences. In some embodiments, the target polynucleotide is a miRNA molecule. In some embodiments, the target polynucleotide is a small target polynucleotide. In some embodiments, the small target polynucleotide can be 25 or fewer nucleotides in length. In some embodiments, the small target polynucleotide can be 23 or fewer nucleotide bases in length. In some embodiments, the target polynucleotide lacks a poly-A tail. In some embodiments, the target polynucleotide is a small DNA molecule derived from a degraded source, such as can be found in for example but not limited to forensics samples (see for example Butler, 2001, *Forensic DNA Typing: Biology and Technology Behind STR Markers*. The target polynucleotides of the present teachings can be derived from any of a number of sources, including without limitation, viruses, prokaryotes, eukaryotes, for example but not limited to plants, fungi, and animals. These sources may include, but are hot limited to, whole blood, a tissue biopsy, lymph, bone marrow, amniotic fluid, hair, skin, semen, biowarfare agents, anal secretions, vaginal secretions, perspiration, saliva, buccal swabs, various environmental samples (for example, agricultural, water, and soil), research samples generally, purified samples generally, cultured cells, and lysed cells. It will be appreciated that target polynucleotides can be isolated from samples using any of a variety of procedures known in the art, for example the Applied Biosystems ABI Prism™ 6100 Nucleic Acid PrepStation, and the ABI Prism™ 6700 Automated Nucleic Acid Workstation, Boom et al., U.S. Pat. No. 5,234, 809., mirVana RNA isolation kit (Ambion), etc, as well as approaches described in U.S. Provisional Application *Pure miRNA Sample Preparation Method*, filed Sep. 12, 2005 to Lao. It will be appreciated that target polynucleotides can be cut or sheared prior to analysis, including the use of such procedures as mechanical force, sonication, restriction endonuclease cleavage, or any method known in the art. In general, the target polynucleotides of the present teachings will be single stranded, though in some embodiments the target polynucleotide can be double stranded, and a single strand can result from denaturation.

As used herein, the term "3' end region of the target polynucleotide" refers to the region of the target to which the 3' target specific portion of the linker probe hybridizes. In some embodiments there can be a gap between the 3' end region of the target polynucleotide and the 5' end of the linker probe, with extension reactions filling in the gap, though generally such scenarios are not preferred because of the likely destabilizing effects on the duplex. In some embodiments, a miRNA molecule is the target, in which case the term "3' end region of the miRNA" is used.

Figure 2A:
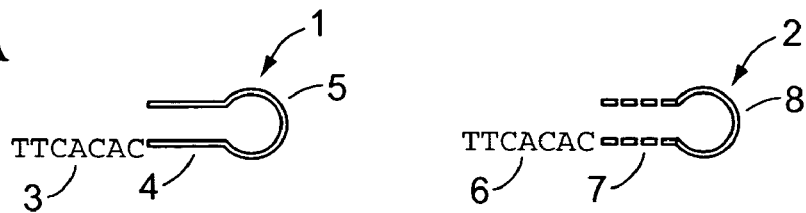
FIG. 2 depicts certain aspects of various compositions as used in various methods according to some embodiments of the present teachings.

As used herein, the term "linker probe" refers to a molecule comprising a 3' target specific portion, a stem, and a loop, that can be extended from its 3' end when hybridized to a corresponding target polynucleotide. Illustrative linker probes are depicted in FIG. 2A, and elsewhere in the present teachings. It will be appreciated that the linker probes, as well as the PCR primers of the present teachings, can be comprised of ribonucleotides, deoxynucleotides, modified ribonucleotides, modified deoxyribonucleotides, modified phosphate-sugar-backbone oligonucleotides, nucleotide analogs, or combinations thereof. For some illustrative teachings of various nucleotide analogs etc, see Fasman, 1989, Practical Handbook of Biochemistry and Molecular Biology, pp. 385-394, CRC Press, Boca Raton, Fla., Loakes, N.A.R. 2001, vol 29:2437-2447, and Pellestor et al., Int J Mol Med. 2004 April; 13(4): 521-5.), references cited therein, and recent articles citing these reviews. It will be appreciated that the selection of the linker probes to query a given target polynucleotide sequence, and the selection of which collection of target polynucleotide sequences to query in a given reaction with which collection of linker probes, will involve procedures generally known in the art, and can involve the use of algorithms to select for those sequences with minimal secondary and tertiary structure, those targets with minimal sequence redundancy with other regions of the genome, those target regions with desirable thermodynamic characteristics, and other parameters desirable for the context at hand.

As used herein, the term "3' target-specific portion" refers to the single stranded portion of a linker probe that is complementary to a target polynucleotide. The 3' target-specific portion is located downstream from the stem of the linker probe. Generally, the 3' target-specific portion is between 6 and 8 nucleotides long. In some embodiments, the 3' target-specific portion is 7 nucleotides long. It will be appreciated that routine experimentation can produce other lengths, and that 3' target-specific portions that are longer than 8 nucleotides or shorter than 6 nucleotides are also contemplated by the present teachings. Generally, the 3'-most nucleotides of the 3' target-specific portion should have minimal complementarity overlap, or no overlap at all, with the 3' nucleotides of the forward primer; it will be appreciated that overlap in these regions can produce undesired primer dimer amplification products in subsequent amplification reactions. In some embodiments, the overlap between the 3'-most nucleotides of the 3' target-specific portion and the 3' nucleotides of the forward primer is 0, 1, 2, or 3 nucleotides. In some embodiments, greater than 3 nucleotides can be complementary between the 3'-most nucleotides of the 3' target-specific portion and the 3' nucleotides of the forward primer, but generally such scenarios will be accompanied by additional non-complementary nucleotides interspersed therein. In some embodiments, modified bases such as LNA can be used in the 3' target specific portion to increase the Tm of the linker probe (see for example Petersen et al., Trends in Biochemistry (2003), 21:2:74-81). In some embodiments, universal bases can be used, for example to allow for smaller libraries of linker probes. Universal bases can also be used in the 3' target specific portion to allow for the detection of unknown targets. For some descriptions of universal bases, see for example Loakes et al., Nucleic Acids Research, 2001, Volume 29, No. 12, 2437-2447. In some embodiments, modifications including but not limited to LNAs and universal bases can improve reverse transcription specificity and potentially enhance detection specificity.

As used herein, the term "stem" refers to the double stranded region of the linker probe that is between the 3' target-specific portion and the loop. Generally, the stem is between 6 and 20 nucleotides long (that is, 6-20 complementary pairs of nucleotides, for a total of 12-40 distinct nucleotides). In some embodiments, the stem is 8-14 nucleotides long. Those in the art will appreciate that stems shorter that 6 nucleotides and longer than 20 nucleotides can be identified in the course of routine methodology and without undue experimentation, and that such shorter and longer stems are contemplated by the present teachings. In some embodiments, the stem can comprise an identifying portion such as a zipcode.

As used herein, the term "loop" refers to a region of the linker probe that is located between the two complementary strands of the stem, as depicted in FIG. 2A and elsewhere in the present teachings. Typically, the loop comprises single stranded nucleotides, though other moieties modified DNA or RNA, Carbon spacers such as C18, and/or PEG (polyethylene glycol) are also possible. Generally, the loop is between 4 and 20 nucleotides long. In some embodiments, the loop is between 14 and 18 nucleotides long. In some embodiments, the loop is 16 nucleotides long. Those in the art will appreciate that loops shorter that 4 nucleotides and longer than 20 nucleotides can be identified in the course of routine methodology and without undue experimentation, and that such shorter and longer loops are contemplated by the present teachings. In some embodiments, the loop can comprise a reverse PCR primer portion.

As used herein, the term "identifying portion" refers to a moiety or moieties that can be used to identify a particular linker probe species, and as a result determine the sample of origin of a target polynucleotide sequence, and can refer to a variety of distinguishable moieties including zipcodes, a known number of nucleobases, and combinations thereof. In some embodiments, an identifying portion, or an identifying portion complement, can hybridize to a detector probe, thereby allowing detection of a target polynucleotide sequence in a decoding reaction. The terms "identifying portion complement" typically refers to at least one oligonucleotide that comprises at least one sequence of nucleobases that are at least substantially complementary to and hybridize with their corresponding identifying portion. Typically, identifying portions and their corresponding identifying portion complements are selected to minimize: internal, self-hybridization; cross-hybridization with different identifying portion species, nucleotide sequences in a reaction composition, including but not limited to gDNA, different species of identifying portion complements, or target-specific portions of probes, and the like; but should be amenable to facile hybridization between the identifying portion and its corresponding identifying portion complement. Identifying portion sequences and identifying portion complement sequences can be selected by any suitable method, for example but not limited to, computer algorithms such as described in PCT Publication Nos. WO 96/12014 and WO 96/41011 and in European Publication No. EP 799,897; and the algorithm and parameters of SantaLucia (Proc. Natl. Acad. Sci. 95:1460-65 (1998)). Descriptions of identifying portions can be found in, among other places, U.S. Pat. No. 6,309,829 (referred to as "tag segment" therein); U.S. Pat. No. 6,451,525 (referred to as "tag segment" therein); U.S. Pat. No. 6,309,829 (referred to as "tag segment" therein); U.S. Pat. No. 5,981,176 (referred to as "grid oligonucleotides" therein); U.S. Pat. No. 5,935,793 (referred to as "identifier tags" therein); and PCT Publication No. WO 01/92579 (referred to as "addressable support-specific sequences" therein). In some embodiments, the stem of the linker probe, the loop of the linker probe, or combinations thereof can comprise an identifying portion, and the detector probe can hybridize to the corresponding identifying portion. In some embodiments, the detector probe can hybridize to both the identifying portion as well as sequence corresponding to the target polynucleotide. In some embodiments, at least two identifying portion: identifying portion complement duplexes have melting temperatures that fall within a $\Delta T_m$ range ($T_{max}$-$T_{min}$) of no more than 10° C. of each other. In some embodiments, at least two identifying portion: identifying portion complement duplexes have melting temperatures that fall within a $\Delta T_m$ range of 5° C. or less of each other. In some embodiments, at least two identifying portion: identifying portion complement duplexes have melting temperatures that fall within a $\Delta T_m$ range of 2° C. or less of each other.

As used herein, the term "extension reaction" refers to an elongation reaction in which the 3' target specific portion of a linker probe is extended to form an extension reaction product comprising a strand complementary to the target polynucleotide. In some embodiments, the target polynucleotide is a miRNA molecule and the extension reaction is a reverse transcription reaction comprising a reverse transcriptase. In some embodiments, the extension reaction is a reverse transcription reaction comprising a polymerase derived from a Eubacteria. In some embodiments, the extension reaction can comprise rTth polymerase, for example as commercially available from Applied Biosystems catalog number N808-0192, and N808-0098. In some embodiments, the target polynucleotide is a miRNA or other RNA molecule, and as such it will be appreciated that the use of polymerases that also comprise reverse transcription properties can allow for some embodiments of the present teachings to comprise a first reverse transcription reaction followed thereafter by an amplification reaction, thereby allowing for the consolidation of two reactions in essentially a single reaction. In some embodiments, the target polynucleotide is a small DNA molecule and the extension reaction comprises a polymerase and results in the synthesis of a $2^{nd}$ strand of DNA. In some embodiments, the consolidation of the extension reaction and a subsequent amplification reaction is further contemplated by the present teachings.

As used herein, the term "primer portion" refers to a region of a polynucleotide sequence that can serve directly, or by virtue of its complement, as the template upon which a primer can anneal for any of a variety of primer nucleotide extension reactions known in the art (for example, PCR). It will be appreciated by those of skill in the art that when two primer portions are present on a single polynucleotide, the orientation of the two primer portions is generally different. For example, one PCR primer can directly hybridize to a first primer portion, while the other PCR primer can hybridize to the complement of the second primer portion. In addition, "universal" primers and primer portions as used herein are generally chosen to be as unique as possible given the particular assays and host genomes to ensure specificity of the assay.

As used herein, the term "forward primer" refers to a primer that comprises an extension reaction product portion and a tail portion. The extension reaction product portion of the forward primer hybridizes to the extension reaction product. Generally, the extension reaction product portion of the forward primer is between 9 and 19 nucleotides in length. In some embodiments, the extension reaction product portion of the forward primer is 16 nucleotides. The tail portion is located upstream from the extension reaction product portion, and is not complementary with the extension reaction product; after a round of amplification however, the tail portion can hybridize to complementary sequence of amplification products. Generally, the tail portion of the forward primer is between 5-8 nucleotides long. In some embodiments, the tail portion of the forward primer is 6 nucleotides long. Those in the art will appreciate that forward primer tail portion lengths shorter than 5 nucleotides and longer than 8 nucleotides can be identified in the course of routine methodology and without undue experimentation, and that such shorter and longer forward primer tail portion lengths are contemplated by the present teachings. Further, those in the art will appreciate that lengths of the extension reaction product portion of the forward primer shorter than 9 nucleotides in length and longer than 19 nucleotides in length can be identified in the course of routine methodology and without undue experimentation, and that such shorter and longer extension reaction product portion of forward primers are contemplated by the present teachings.

As used herein, the term "reverse primer" refers to a primer that when extended forms a strand complementary to the target polynucleotide. In some embodiments, the reverse primer corresponds with a region of the loop of the linker probe. Following the extension reaction, the forward primer can be extended to form a second strand product. The reverse primer hybridizes with this second strand product, and can be extended to continue the amplification reaction. In some embodiments, the reverse primer corresponds with a region of the loop of the linker probe, a region of the stem of the linker probe, a region of the target polynucleotide, or combinations thereof. Generally, the reverse primer is between 13-16 nucleotides long. In some embodiments the reverse primer is 14 nucleotides long. In some embodiments, the reverse primer can further comprise a non-complementary tail region, though such a tail is not required. In some embodiments, the reverse primer is a "universal reverse primer," which indicates that the sequence of the reverse primer can be used in a plurality of different reactions querying different target polynucleotides, but that the reverse primer nonetheless is the same sequence.

The term "upstream" as used herein takes on its customary meaning in molecular biology, and refers to the location of a region of a polynucleotide that is on the 5' side of a "downstream" region. Correspondingly, the term "downstream" refers to the location of a region of a polynucleotide that is on the 3' side of an "upstream" region.

As used herein, the term "hybridization" refers to the complementary base-pairing interaction of one nucleic acid with another nucleic acid that results in formation of a duplex, triplex, or other higher-ordered structure, and is used herein interchangeably with "annealing." Typically, the primary interaction is base specific, e.g., A/T and G/C, by Watson/Crick and Hoogsteen-type hydrogen bonding. Base-stacking and hydrophobic interactions can also contribute to duplex stability. Conditions for hybridizing detector probes and primers to complementary and substantially complementary target sequences are well known, e.g., as described in Nucleic Acid Hybridization, A Practical Approach, B. Hames and S. Higgins, eds., IRL Press, Washington, D.C. (1985) and J. Wetmur and N. Davidson, Mol. Biol. 31:349 et seq. (1968). In general, whether such annealing takes place is influenced by, among other things, the length of the polynucleotides and the complementary, the pH, the temperature, the presence of mono- and divalent cations, the proportion of G and C nucleotides in the hybridizing region, the viscosity of the medium, and the presence of denaturants. Such variables influence the time required for hybridization. Thus, the preferred annealing conditions will depend upon the particular application. Such conditions, however, can be routinely determined by the person of ordinary skill in the art without undue experimentation. It will be appreciated that complementarity need not be perfect; there can be a small number of base pair mismatches that will minimally interfere with hybridization between the target sequence and the single stranded nucleic acids of the present teachings. However, if the number of base pair mismatches is so great that no hybridization can occur under minimally stringent conditions then the sequence is generally not a complementary target sequence. Thus, complementarity herein is meant that the probes or primers are sufficiently complementary to the target sequence to hybridize under the selected reaction conditions to achieve the ends of the present teachings.

As used herein, the term "amplifying" refers to any means by which at least a part of a target polynucleotide, target polynucleotide surrogate, or combinations thereof, is reproduced, typically in a template-dependent manner, including without limitation, a broad range of techniques for amplifying nucleic acid sequences, either linearly or exponentially. Exemplary procedures for performing an amplifying step include the polymerase chain reaction (PCR). Descriptions of additional techniques that can be used in the present teachings can be found in, among other places, Sambrook et al. Molecular Cloning, 3$^{rd}$ Edition; Ausbel et al.; PCR Primer: A Laboratory Manual, Diffenbach, Ed., Cold Spring Harbor Press (1995); The Electronic Protocol Book, Chang Bioscience (2002), Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February; 4(1):41-7, U.S. Pat. No. 6,027,998; U.S. Pat. No. 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18-(2002); Lage et al., Genome Res. 2003 February; 13(2):294-307, and Landegren et al., Science 241:1077-80 (1988), Demidov, V., Expert Rev Mol Diagn. 2002 November; 2(6):542-8., Cook et al., J Microbiol Methods. 2003 May; 53(2):165-74, Schweitzer et al., Curr Opin Biotechnol. 2001 February; 12(1):21-7, U.S. Pat. No. 5,830,711, U.S. Pat. No. 6,027,889, U.S. Pat. No. 5,686,243, Published P.C.T. Application W00056927A3, and Published P.C.T. Application WO9803673A1. In some embodiments, newly-formed nucleic acid duplexes are not initially denatured, but are used in their double-stranded form in one or more subsequent steps. An extension reaction is an amplifying technique that comprises elongating a linker probe that is annealed to a template in the 5' to 3' direction using an amplifying means such as a polymerase and/or reverse transcriptase. According to some embodiments, with appropriate buffers, salts, pH, temperature, and nucleotide triphosphates, including analogs thereof, i.e., under appropriate conditions, a polymerase incorporates nucleotides complementary to the template strand starting at the 3'-end of an annealed linker probe, to generate a complementary strand. In some embodiments, the polymerase used for extension lacks or substantially lacks 5' exonuclease activity. In some embodiments of the present teachings, unconventional nucleotide bases can be introduced into the amplification reaction products and the products treated by enzymatic (e.g., glycosylases) and/or physical-chemical means in order to render the product incapable of acting as a template for subsequent amplifications. In some embodiments, uracil can be included as a nucleobase in the reaction mixture, thereby allowing for subsequent reactions to decontaminate carryover of previous uracil-containing products by the use of uracil-N-glycosylase (see for example Published P.C.T. Application WO9201814A2). In some embodiments of the present teachings, any of a variety of techniques can be employed prior to amplification in order to facilitate amplification success, as described for example in Radstrom et al., Mol Biotechnol. 2004 February; 26(2):133-46. In some embodiments, amplification can be achieved in a self-contained integrated approach comprising sample preparation and detection, as described for example in U.S. Pat. Nos. 6,153,425 and 6,649,378. Reversibly modified enzymes, for example but not limited to those described in U.S. Pat. No. 5,773,258, are also within the scope of the disclosed teachings. The present teachings also contemplate various uracil-based decontamination strategies, wherein for example uracil can be incorporated into an amplification reaction, and subsequent carry-over products removed with various glycosylase treatments (see for example U.S. Pat. No. 5,536,649, and U.S. Provisional Application 60/584,682 to Andersen et al.,). Those in the art will understand that any protein with the desired enzymatic activity can be used in the disclosed methods and kits. Descriptions of DNA polymerases, including reverse transcriptases, uracil N-glycosylase, and the like, can be found in, among other places, Twyman, Advanced Molecular Biology, BIOS Scientific Publishers, 1999; Enzyme Resource Guide, rev. 092298, Promega, 1998; Sambrook and Russell; Sambrook et al.; Lehninger; PCR: The Basics; and Ausbel et al.

As used herein, the term "detector probe" refers to a molecule used in an amplification reaction, typically for quantitative or real-time PCR analysis, as well as end-point analysis. Such detector probes can be used to monitor the amplification of the target polynucleotide. In some embodiments, detector probes present in an amplification reaction are suitable for monitoring the amount of amplicon(s) produced as a function of time. Such detector probes include, but are not limited to, the 5'-exonuclease assay (TaqMan® probes described herein (see also U.S. Pat. No. 5,538,848) various stem-loop molecular beacons (see e.g., U.S. Pat. Nos. 6,103,476 and 5,925,517 and Tyagi and Kramer, 1996, Nature Biotechnology 14:303-308), stemless or linear beacons (see, e.g., WO 99/21881), PNA Molecular Beacons™ (see, e.g., U.S. Pat. Nos. 6,355,421 and 6,593,091), linear PNA beacons (see, e.g., Kubista et al., 2001, SPIE 4264:53-58), non-FRET probes (see, e.g., U.S. Pat. No. 6,150,097), Sunrise®/Amplifluor® probes (U.S. Pat. No. 6,548,250), stem-loop and duplex Scorpion™ probes (Solinas et al., 2001, Nucleic Acids Research 29:E96 and U.S. Pat. No. 6,589,743), bulge loop probes (U.S. Pat. No. 6,590,091), pseudo knot probes (U.S. Pat. No. 6,589,250), cyclicons (U.S. Pat. No. 6,383,752), MGB Eclipse™ probe (Epoch Biosciences), hairpin probes (U.S. Pat. No. 6,596,490), peptide nucleic acid (PNA) light-up probes, self-assembled nanoparticle probes, and ferrocene-modified probes described, for example, in U.S. Pat. No. 6,485,901; Mhlanga et al., 2001, Methods 25:463-471; Whitcombe et al., 1999, Nature Biotechnology. 17:804-807; Isacsson et al., 2000, Molecular Cell Probes. 14:321-328; Svanvik et al., 2000, Anal Biochem. 281:26-35; Wolffs et al., 2001, Biotechniques 766:769-771; Tsourkas et al., 2002, Nucleic Acids Research. 30:4208-4215; Riccelli et al., 2002, Nucleic Acids Research 30:4088-4093; Zhang et al., 2002 Shanghai. 34:329-332; Maxwell et al., 2002, J. Am. Chem. Soc. 124:9606-9612; Broude et al., 2002, Trends Biotechnol. 20:249-56; Huang et al., 2002, Chem Res. Toxicol. 15:118-126; and Yu et al., 2001, J. Am. Chem. Soc 14:11155-11161. Detector probes can also comprise quenchers, including without limitation black hole quenchers (Biosearch), Iowa Black (IDT), QSY quencher (Molecular Probes), and Dabsyl and Dabcel sulfonate/carboxylate Quenchers (Epoch). Detector probes can also comprise two probes, wherein for example a fluor is on one probe, and a quencher is on the other probe, wherein hybridization of the two probes together on a target quenches the signal, or wherein hybridization on the target alters the signal signature via a change in fluorescence. Detector probes can also comprise sulfonate derivatives of fluorescenin dyes with SO3 instead of the carboxylate group, phosphoramidite forms of fluorescein, phosphoramidite forms of CY 5 (commercially available for example from Amersham). In some embodiments, interchelating labels are used such as ethidium bromide, SYBR® Green I (Molecular Probes), and PicoGreen® (Molecular Probes), thereby allowing visualization in real-time, or end point, of an amplification product in the absence of a detector probe. In some embodiments, real-time visualization can comprise both an intercalating detector probe and a sequence-based detector probe can be employed. In some embodiments, the detector probe is at least partially quenched when not hybridized to a complementary sequence in the amplification reaction, and is at least partially unquenched when hybridized to a complementary sequence in the amplification reaction. In some embodiments, the detector probes of the present teachings have a Tm of 63-69 C, though it will be appreciated that guided by the present teachings routine experimentation can result in detector probes with other Tms. In some embodiments, probes can further comprise various modifications such as a minor groove binder (see for example U.S. Pat. No. 6,486,308) to further provide desirable thermodynamic characteristics. In some embodiments, detector probes can correspond to identifying portions or identifying portion complements. In some embodiments, the identifying portions or identifying portion complements, and the corresponding detector probes can vary by only two nucleotides. For example, a first identifying portion encoding a sample A can differ from a second identifying portion encoding a sample B by only two nucleotide bases. Correspondingly, the two detector probes can differ from one another by only two nucleotide bases. Such a configuration can minimize unwanted variation between the activity of the two detector probes, thus improving the ability to accurately quantify the expression level difference between a given target polynucleotide between the two samples. In some embodiments, the detector probes can differ from each other by as little as a single nucleotide. In some embodiments, the detector probes can differ by three nucleotides. In some embodiments, the detector probes can differ by four nucleotides.

The term "corresponding" as used herein refers to a specific relationship between the elements to which the term refers. Some non-limiting examples of corresponding include: a linker probe can correspond with a target polynucleotide, and vice versa. A forward primer can correspond with a target polynucleotide, and vice versa. A linker probe can correspond with a forward primer for a given target polynucleotide, and vice versa. The 3' target-specific portion of the linker probe can correspond with the 3' region of a target polynucleotide, and vice versa. A detector probe can correspond with a particular region of a target polynucleotide and vice versa. A detector probe can correspond with a particular identifying portion and vice versa. In some cases, the corresponding elements can be complementary. In some cases, the corresponding elements are not complementary to each other, but one element can be complementary to the complement of another element.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, the term "reaction vessel" generally refers to any container in which a reaction can occur in accordance with the present teachings. In some embodiments, a reaction vessel can be an eppendorf tube, and other containers of the sort in common practice in modern molecular biology laboratories. In some embodiments, a reaction vessel can be a well in microtitre plate, a spot on a glass slide, or a well in an Applied Biosystems TaqMan Low Density Array for gene expression (formerly MicroCard™) For example, a plurality of reaction vessels can reside on the same support. In some embodiments, lab-on-a-chip like devices, available for example from Caliper and Fluidgm, can provide for reaction vessels. In some embodiments, various microfluidic approaches as described in U.S. application Ser. No. 11/059,824 to Wenz et al., can be employed. It will be recognized that a variety of reaction vessel are available in the art and within the scope of the present teachings.

As used herein, the term "detection" refers to any of a variety of ways of determining the presence and/or quantity and/or identity of a target polynucleoteide. In some embodiments employing a donor moiety and signal moiety, one may use certain energy-transfer fluorescent dyes. Certain nonlimiting exemplary pairs of donors (donor moieties) and acceptors (signal moieties) are illustrated, e.g., in U.S. Pat. Nos. 5,863,727; 5,800,996; and 5,945,526. Use of some combinations of a donor and an acceptor have been called FRET (Fluorescent Resonance Energy Transfer). In some embodiments, fluorophores that can be used as signaling probes include, but are not limited to, rhodamine, cyanine 3 (Cy 3), cyanine 5 (Cy 5), fluorescein, Vic™, Liz™, Tamra™, 5-Fam™, 6-Fam™, and Texas Red (Molecular Probes). (Vic™, Liz™, Tamra™, 5-Fam™, and 6-Fam™ (all available from Applied Biosystems, Foster City, Calif.). In some embodiments, the amount of detector probe that gives a fluorescent signal in response to an excited light typically relates to the amount of nucleic acid produced in the amplification reaction. Thus, in some embodiments, the amount of fluorescent signal is related to the amount of product created in the amplification reaction. In such embodiments, one can therefore measure the amount of amplification product by measuring the intensity of the fluorescent signal from the fluorescent indicator. According to some embodiments, one can employ an internal standard to quantify the amplification product indicated by the fluorescent signal. See, e.g., U.S. Pat. No. 5,736,333. Devices have been developed that can perform a thermal cycling reaction with compositions containing a fluorescent indicator, emit a light beam of a specified wavelength, read the intensity of the fluorescent dye, and display the intensity of fluorescence after each cycle. Devices comprising a thermal cycler, light beam emitter, and a fluorescent signal detector, have been described, e.g., in U.S. Pat. Nos. 5,928,907; 6,015,674; and 6,174,670, and include, but are not limited to the ABI Prism® 7700 Sequence Detection System (Applied Biosystems, Foster City, Calif.), the ABI GeneAmp® 5700 Sequence Detection System (Applied Biosystems, Foster City, Calif.), the ABI GeneAmp® 7300 Sequence Detection System (Applied Biosystems, Foster City, Calif.), and the ABI GeneAmp® 7500 Sequence Detection System (Applied Biosystems). In some embodiments, each of these functions can be performed by separate devices. For example, if one employs a Q-beta replicase reaction for amplification, the reaction may not take place in a thermal cycler, but could include a light beam emitted at a specific wavelength, detection of the fluorescent signal, and calculation and display of the amount of amplification product. In some embodiments, combined thermal cycling and fluorescence detecting devices can be used for precise quantification of target nucleic acid sequences in samples. In some embodiments, fluorescent signals can be detected and displayed during and/or after one or more thermal cycles, thus permitting monitoring of amplification products as the reactions occur in "real time." In some embodiments, one can use the amount of amplification product and number of amplification cycles to calculate how much of the target nucleic acid sequence was in the sample prior to amplification. In some embodiments, one could simply monitor the amount of amplification product after a predetermined number of cycles sufficient to indicate the presence of the target nucleic acid sequence in the sample. One skilled in the art can easily determine, for any given sample type, primer sequence, and reaction condition, how many cycles are sufficient to determine the presence of a given target polynucleotide. As used herein, determining the presence of a target can comprise identifying it, as well as optionally quantifying it. In some embodiments, the amplification products can be scored as positive or negative as soon as a given number of cycles is complete. In some embodiments, the results may be transmitted electronically directly to a database and tabulated. Thus, in some embodiments, large numbers of samples can be processed and analyzed with less time and labor when such an instrument is used. In some embodiments, different detector probes may distinguish between different target polynucleoteides. A non-limiting example of such a probe is a 5'-nuclease fluorescent probe, such as a TaqMan® probe molecule, wherein a fluorescent molecule is attached to a fluorescence-quenching molecule through an oligonucleotide link element. In some embodiments, the oligonucleotide link element of the 5'-nuclease fluorescent probe binds to a specific sequence of an identifying portion or its complement. In some embodiments, different 5'-nuclease fluorescent probes, each fluorescing at different wavelengths, can distinguish between different amplification products within the same amplification reaction. For example, in some embodiments, one could use two different 5'-nuclease fluorescent probes that fluoresce at two different wavelengths ($WL_A$ and $WL_B$) and that are specific to two different stem regions of two different extension reaction products (A' and B', respectively). Amplification product A' is formed if target nucleic acid sequence A is in the sample, and amplification product B' is formed if target nucleic acid sequence B is in the sample. In some embodiments, amplification product A' and/or B' may form even if the appropriate target nucleic acid sequence is not in the sample, but such occurs to a measurably lesser extent than when the appropriate target nucleic acid sequence is in the sample. After amplification, one can determine which specific target nucleic acid sequences are present in the sample based on the wavelength of signal detected and their intensity. Thus, if an appropriate detectable signal value of only wavelength $WL_A$ is detected, one would know that the sample includes target nucleic acid sequence A, but not target nucleic acid sequence B. If an appropriate detectable signal value of both wavelengths $WL_A$ and $WL_B$ are detected, one would know that the sample includes both target nucleic acid sequence A and target nucleic acid sequence B. In some embodiments, detection can occur through any of a variety of mobility dependent analytical techniques based on differential rates of migration between different analyte species. Exemplary mobility-dependent analysis techniques include electrophoresis, chromatography, mass spectroscopy, sedimentation, e.g., gradient centrifugation, field-flow fractionation, multi-stage extraction techniques, and the like. In some embodiments, mobility probes can be hybridized to amplification products, and the identity of the target polynucleotide determined via a mobility dependent analysis technique of the eluted mobility probes, as described for example in Published P.C.T. Application WO04/46344 to Rosenblum et al., and WO01/92579 to Wenz et al.,.. In some embodiments, detection can be achieved by various microarrays and related software such as the Applied Biosystems Array System with the Applied Biosystems 1700 Chemiluminescent Microarray Analyzer and other commercially available array systems available from Affymetrix, Agilent, Illumina, and Amersham Biosciences, among others (see also Gerry et al., J. Mol. Biol. 292:251-62, 1999; De Bellis et al., Minerva Biotec 14:247-52, 2002; and Stears et al., Nat. Med. 9:140-45, including supplements, 2003). It will also be appreciated that detection can comprise reporter groups that are incorporated into the reaction products, either as part of labeled primers or due to the incorporation of labeled dNTPs during an amplification, or attached to reaction products, for example but not limited to, via hybridization tag complements comprising reporter groups or via linker arms that are integral or attached to reaction products. Detection of unlabeled reaction products, for example using mass spectrometry, is also within the scope of the current teachings.

EXEMPLARY EMBODIMENTS

FIG. 1 depicts an overview of certain methods according to the present teachings. Here, a first sample (A) and a second sample (B) are depicted in separate reaction vessels. The first reaction vessel can contain target polynucleotides (for example micro RNAs) from sample A and the second reation can contain micro RNAs from sample B. For example, sample A can be derived from a wild-type biological source, and sample B can be derived from a mutant biological source. Following a treatment such as a reverse transcription reaction to convert the micro RNAs in sample A into extension products and the micro RNAs in sample B into extension products, the two samples can be mixed together into a single reaction vessel comprising A+B. A collection of decoding reactions can then be performed to compare the expression levels of micro RNAs between the two samples, using for example real-time PCR on a microfluidic card, or detection by end-point PCR followed by a hybridization array.

Figure 2B:
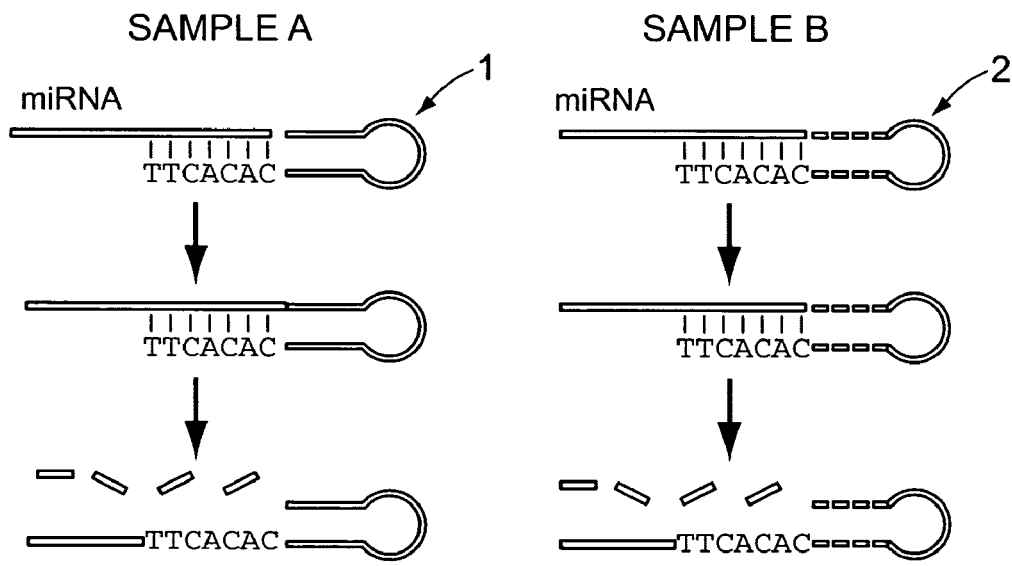

FIG. 2A depicts certain compositions according to some embodiments of the present teachings. Here, a first linker probe (1) is depicted, illustrating a 3' target specific portion (3), a stem (4), and a loop (5). Also, a second linker probe (2) is depicted, illustrating a 3' target specific portion (6), a stem (7), and a loop (8). Of note, the stem of the first linker probe (4) is depicted as a solid line, while the stem of the second linker probe (7) is depicted as dashed line, indicating that the sequence of the stem of the first linker probe is different from the sequence of the stem of the second linker probe. Accordingly, the stem sequence can considered a zipcode. Thus, the identity of sample A can be encoded, for example, with a first zipcode sequence located in the stem of the first linker probe, and the identity of sample B can be encoded with a second zipcode sequence located in the stem of the second linker probe. The loop of the first linker probe and the loop of the second linker probe can comprise the same sequence, which can encode a universal reverse primer In FIG. 2B (top), a miRNA from a sample A is hybridized to the first linker probe (1) in a first reaction vessel, and a miRNA from a sample B is hybridized to the second linker probe (2) in a second reaction vessel. The species of miRNA from sample A can be considered the same as the species of miRNA from sample B. Accordingly, the sequence of the 3' target specific portion of the first linker probe (shown as TTCACAC) is the same as the 3' target specific portion of the second linker probe (also shown as TTCACAC). Following hybridization of the first linker probe to the miRNA in the first reaction vessel and hybridization of the second linker probe to the miRNA in the second reaction vessel, one or more downstream reactions can be performed. For example, in some embodiments of the present teachings, the linker probes are ligated to the miRNA molecules in a ligation reaction (middle). The ligation products are then subjected to an extension reaction, wherein an enzyme such as a polymerase and/or reverse transcriptase is employed to extend the 3' end of the linker probe to form a strand complementary to the target polynucleotide. In some embodiments, the linker probes are not ligated to the miRNA molecules, and an extension reaction is performed on the hybridized linker probe/miRNA complex. Following the generation of an extension reaction product in each of the two reaction vessels, a subsequent heating step can degrade the RNA component of the molecule, leaving the newly synthesized strand of nucleic acid in tact (bottom).

Figure 2C:
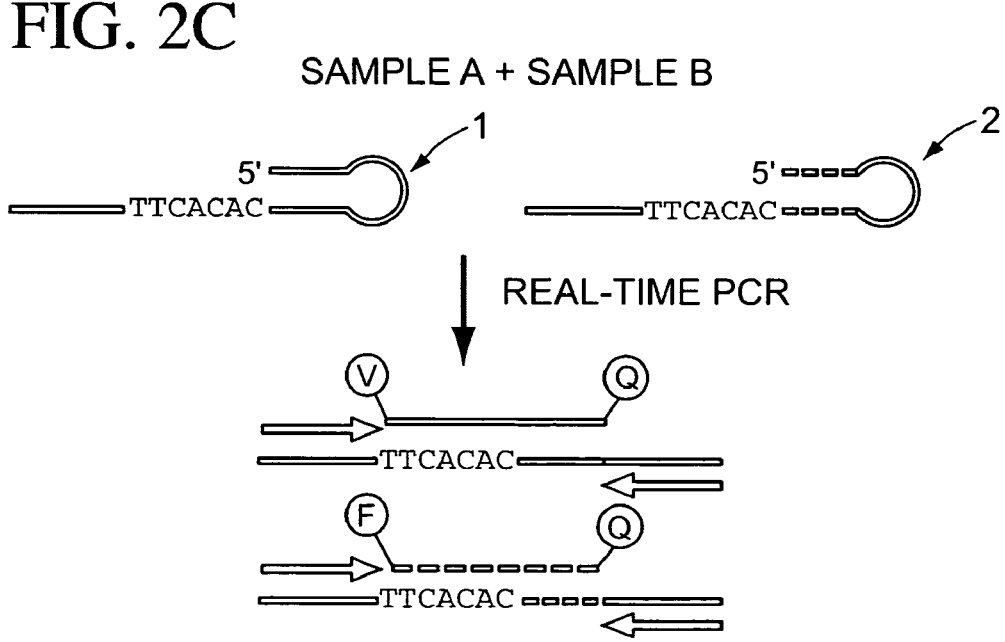

As shown in FIG. 2C, the extension products from sample A bearing the first linker probe (1), and the extension products from sample B bearing the second linker probe (2), can be mixed together, and a real-time PCR such as TaqMan™ performed. Here, a first detector probe in the PCR is depicted as solid line with a label (V, indicating the florophore Vic) and a quencher (Q). This first detector probe is designed to query the miRNA extension product from sample A. Further, a second detector probe in the PCR is depicted as dashed line with a label (F, indicating the florophore Fam) and a quencher (Q). This second detector probe is designed to query the miRNA extension product from sample B. A miRNA specific forward primer and a universal reverse primer are included in the PCR. Thus a single primer pair can be used to ampify the miRNA from sample A and sample B. The difference in signal between the first detector probe and the second detector probe can be used to quantify the difference in expression level of the miRNA between sample A and sample B in the real time PCR.

It will be appreciated that in some embodiments of the present teachings, the loop can correspond to the reverse primer. In some embodiments, the detector probe can correspond with a region of the amplification product corresponding with the 3' end region of the target polynucleotide in the amplification product, as well as a region upstream from the 3' end region of the target polynucleotide in the amplification product, as well as the linker probe stem in the amplification product. In some embodiments, the upstream region of the stem, as well as the loop, can correspond to the reverse primer. In some embodiments the detector probe can correspond with the linker probe stem in the amplification product. In some embodiments, the upstream region of the stem, as well as the loop can correspond to the reverse primer. It will be appreciated that various related strategies for implementing the different functional regions of these compositions are possible in light of the present teachings, and that such derivations are routine to one having ordinary skill in the art without undue experimentation. Further illustrative design characteristics of linker probes can be found in FIG. 2 of U.S. Non-Provisional application Ser. No. 10/947,460 to Chen et al.

In some embodiments of the present teachings as depicted in FIG. 2, an end point assay can be performed rather than a real-time assay. For example, the ratio of Fam/Vic Rn values can determine the relative abundance of a miRNA in a Sample A as compared to a sample B.

Figure 3A:
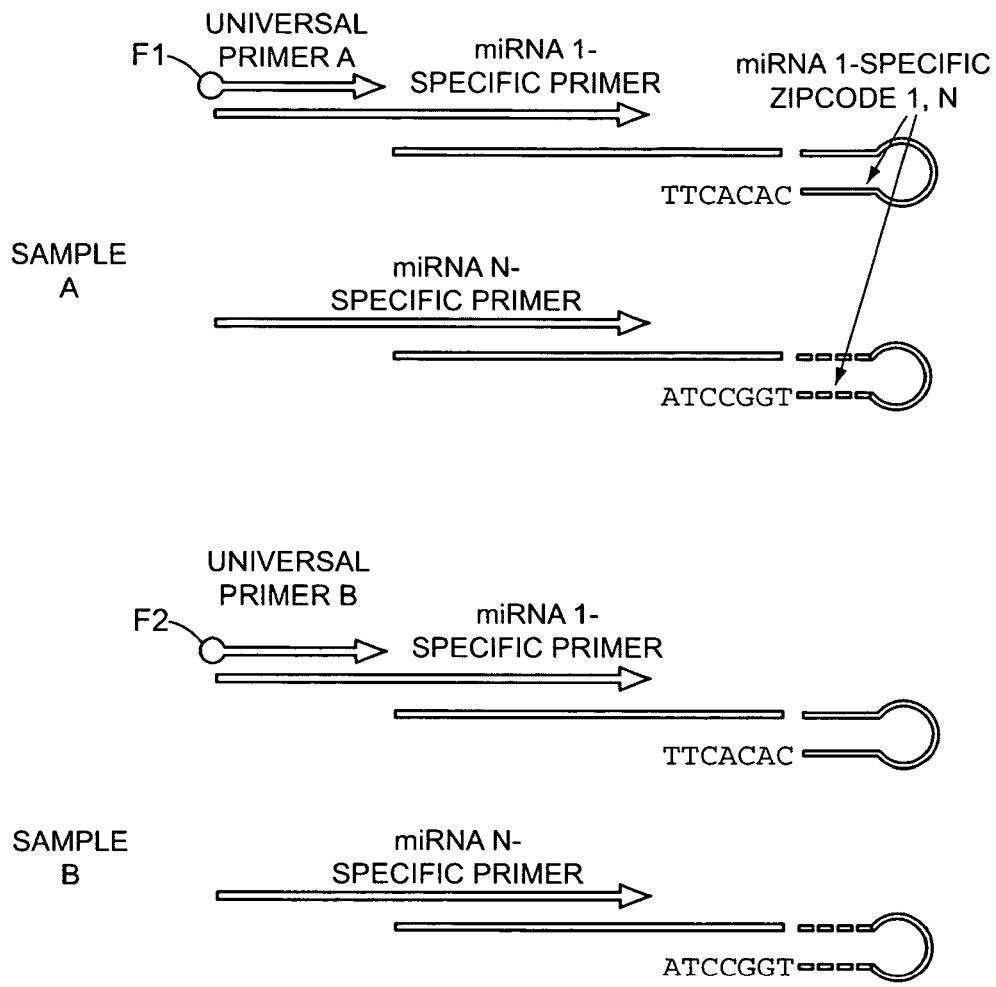
FIG. 3 depicts certain methods according to some embodiments of the present teachings.
Figure 3B:
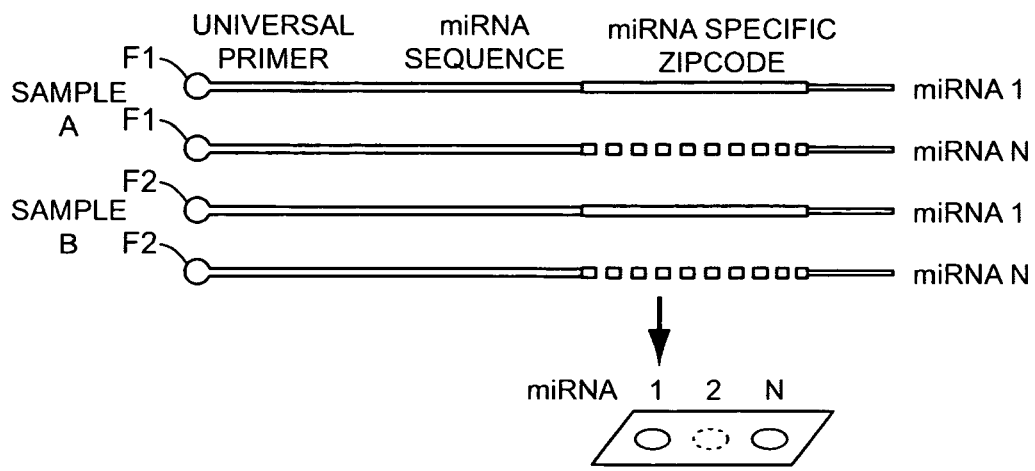

In FIG. 3, an approach for querying miRNAs in two samples is depicted with a microarray read-out. As shown in FIG. 3A, the stem of the top linker probe can encode a zipcode 1, whereas the stem of the bottom linker probe can encode a zipcode N. Thus, a plurality of different miRNA species 1-N can be encoded with a plurality of different zipcodes 1-N. Further, the sample of origin (A) of a first plurality of miRNAs can be encoded by a universal primer A portion in the tail of each forward primer, and the sample of origin (B) of a second plurality of miRNAs can be encoded by a universal primer B portion in the tail of each forward primer. In this situation, an encoding PCR for sample A is performed in a reaction vessel that is separate from the reaction vessel in which an encoding PCR for sample B is performed. Each encoding PCR comprises a plurality of target specific forward primers bearing their appropriate universal tail, as well a reverse primer that was encoded in the loop of the linker probe. A secondary PCR can then be performed in which sample A and sample are mixed together. A universal primer A labeled with a distinct label (F1-florophore 1) will extend those targets derived from sample A, and a universal primer labeled with a different distinct label (F2-florophore 2) will extend those targets derived from sample B. Procedures for ensuring similar Tm characteristics and minimal cross-hybridization of primer A and primer B will be undertaken to preserve the specificity of the reaction. The resulting combined labeled PCR amplicons can then be hybridized to a microarray for decoding. Here, the microarray comprises spots with the corresponding complementary zipcode sequences. Thus, a given spot will produce hybridization for a given species of target polynucleotide. The ratio of signal from F1 to F2 gives a measure of the difference in expression level for a given target polynucleotide between the two samples.

The present teachings also contemplate reactions comprising configurations other than a linker probe. For example, in some embodiments, two hybridized molecules with a sticky end can be employed, wherein for example an overlapping 3' sticky end hybridizes with the 3' end region of the target polynucleotide. Some descriptions of two molecule configurations that can be employed in the present teachings can be found in Chen et al., U.S. Non-Provisional application Ser. No. 10/982,619. Viewed in light of the present teachings herein, one of skill in the art will appreciate that the approaches of Ser. No. 10/982,619 can also be employed to result in extension reaction products that are longer that the target polynucleotide. These longer products can be detected with detector probes by, for example, taking advantage of the additional nucleotides introduced into the reaction products.

Generally however, the loop structure of the present teachings will enhance the Tm of the target polynucleotide-linker probe duplex. Without being limited to any particular theory, this enhanced Tm could possibly be due to base stacking effects. Also, the characteristics of the linker probe of the present teachings can minimize nonspecific priming during the extension reaction, and/or a subsequent amplification reaction such as PCR. Further, the linker probe of the present teachings can better differentiate mature and precursor forms of miRNA.

The present teachings specifically contemplate embodiments wherein the linker probe is ligated to the target polynucleotide, as well as embodiments in which the linker probe is hybridized buy not ligated to the target polynucleotide, as described for example in Chen et al., U.S. Non-Provisional application Ser. No. 10/947,460.

The present teachings also contemplate encoding and decoding reaction schemes, wherein a first encoding extension reaction is followed by a second decoding amplification reaction, as described for example in Andersen et al., U.S.

Non-Provisional application Ser. No. 11/090,830, and Lao et al., U.S. Provisional application Ser. No. 11/090,468.

The present teachings also contemplate a variety of strategies to minimize the number of different molecules in multiplexed amplification strategies, as described for example in Whitcombe et al., U.S. Pat. No. 6,270,967.

Additional strategies for using the linker probes of the present teachings in the context of single step assays, as well as in the context of small primer compositions, can be found in filed U.S. Non-Provisional application Ser. No. 10/944,153 to Lao and Straus, as well as in Elfaitouri et al., J. Clin. Virol. 2004, 30(2): 150-156.

Various contexts in which the present teachings can be employed for discovery of novel biomarkers for cancer diagnosis and stem cell differentiation can found in U.S. Provisional Application 60/686,274 to Bloch et al.

Kits

In certain embodiments, the present teachings also provide kits designed to expedite performing certain methods. In some embodiments, kits serve to expedite the performance of the methods of interest by assembling two or more components used in carrying out the methods. In some embodiments, kits may contain components in pre-measured unit amounts to minimize the need for measurements by end-users. In some embodiments, kits may include instructions for performing one or more methods of the present teachings. In certain embodiments, the kit components are optimized to operate in conjunction with one another.

For example, the present teachings provide a kit comprising, a reverse transcriptase, a first linker probe in a first reaction vessel, and a second linker probe in a second reaction vessel, wherein the first linker probe comprises a stem, a loop, and a 3' target-specific portion, wherein the 3' target-specific portion corresponds to a miRNA, and the stem encodes a first identifying portion such as a zipcode that encodes the identity of a first sample of origin, and wherein the second linker probe comprises a stem, a loop, and a 3' target-specific portion, wherein the 3' target-specific portion corresponds to a miRNA, and the stem encodes a second identifying portion such as a zipcode that encodes the identity of a second sample of origin. In some embodiments, the kits can comprise a DNA polymerase. In some embodiments, the kits can comprise a primer pair. In some embodiments, the kits can further comprise a forward primer specific for a miRNA, and, a universal reverse primer, wherein the universal reverse primer comprises a nucleotide of the loop of the linker probe. In some embodiments, the kits can comprise a plurality of primer pairs, wherein each primer pair is in one reaction vessel of a plurality of reaction vessels. In some embodiments, the kits can comprise a first detector probe and a second detector probe. In some embodiments, the first detector probe comprises a nucleotide of the first identifying portion in the first linker probe stem in the amplification product or a nucleotide of the first linker probe stem complement in the amplification product, and the first detector probe further comprises a nucleotide of the 3' end region of the miRNA in the amplification product or a nucleotide of the 3' end region of the miRNA complement in the amplification product. In some embodiments, the second detector probe comprises a nucleotide of the second identifying portion in the second linker probe stem in the amplification product or a nucleotide of the second linker probe stem complement in the amplification product, and the second detector probe further comprises a nucleotide of the 3' end region of the miRNA in the amplification product or a nucleotide of the 3' end region of the miRNA complement in the amplification product.

The present teachings further contemplate kits comprising a means for hybridizing, a means for ligation, a means for extending, a means for amplifying, a means for detecting, or combinations thereof.

While the present teachings have been described in terms of these exemplary embodiments, the skilled artisan will readily understand that numerous variations and modifications of these exemplary embodiments are possible without undue experimentation. All such variations and modifications are within the scope of the current teachings. Aspects of the present teachings may be further understood in light of the following examples, which should not be construed as limiting the scope of the teachings in any way.

EXAMPLE

A single-plex reaction can be performed on a collection of mouse miRNAs from a brain sample and a liver sample to compare the expression level of a miRNA target polynucleotide.

First, two parallel 6 ul reactions are set up comprising: 1 ul Reverse Transcription Enzyme Mix (Applied Biosystems part number 4340444), 0.5 ul dH20, 0.25 ul 2M KCl, 0.05 ul dNTPs (25 mM each), 1 ul 10×RT buffer, 0.25 ul Applied Biosystems RNase Inhibitor (10 units/ul), and 2.2 ul dH20. Next, 2 ul of the first linker probe (0.25 uM) and RNA samples (2 ul of 0.25 ug/ul mouse liver total RNA (Ambion, product number 7810)) are added to the first reaction, and, 2 ul of the second linker probe (0.25 uM) and RNA samples (2 ul of 0.25 ug/ul mouse brain total RNA (Ambion, product number 7812)) are added to the second reaction. Next, each reaction is mixed, spun briefly, and placed on ice for 5 minutes. Each reaction is then incubated at 42 C for 30 minutes, followed by 85 C for 5 minutes, and then held at 4 C. The reactions are then mixed together, and diluted 4 times by adding 30 ul of dH20 prior to the PCR amplification.

A 10 ul PCR amplification is then set up comprising: 2 ul of diluted reverse transcription reaction product, 1.3 ul 10 uM miRNA specific Forward Primer, 0.7 ul 10 uM Universal Reverse Primer, 0.2 ul first TaqMan detector probe, 0.2 ul second TaqMan detector probe, 0.2 ul dNTPs (25 mM each), 0.6 ul dH20, 5 ul 2× TaqMan master mix (Applied Biosystems, without UNG). The reaction is started with a 95 C step for 10 minutes. Then, 40 cycles are performed, each cycle comprising 95 C for 15 seconds, and 60 C for 1 minute. Comparison of the signal from the first Taqman detector probe to the second TaqMan detector probe give a measure of the difference in expression level for the micro RNA of interest.

Illustrative designs for various primers and probes applicable to the present teachings can be found in U.S. Non-Provisional application Ser. No. 10/947,460, including Table 2.

Although the disclosed teachings have been described with reference to various applications, methods, kits, and compositions, it will be appreciated that various changes and modifications may be made without departing from the teachings herein. The foregoing examples are provided to better illustrate the disclosed teachings and are not intended to limit the scope of the teachings herein.

We claim:

1. A method for quantifying a small target polynucleotide in each of two samples comprising;

providing a first reaction mixture comprising a small target polynucleotide from a first sample, and a first linker probe, wherein the first linker probe comprises a 3' target-specific portion, a stem, and a loop, wherein the 3' target-specific portion base pairs with the 3' end of the target polynucleotide;

providing a second reaction mixture comprising a small target polynucleotide from a second sample, and a second linker probe, wherein the second linker probe comprises a 3' target-specific portion, a stem, and a loop, wherein the 3' target-specific portion base pairs with the 3' end of the target polynucleotide, wherein the small target polynucleotide in the first reaction mixture is the same species as the small target polynucleotide in the second reaction mixture;

hybridizing the first linker probe to the small target polynucleotide in the first reaction mixture to form a first target-linker probe complex, and extending the first linker probe to form a first extension product;

hybridizing the second linker probe to the small target polynucleotide in the second reaction mixture to form a second target-linker probe complex, and extending the second linker probe to form a second extension product;

combining the first extension reaction product and the second extension reaction product to form a pooled reaction mixture;

PCR amplifying the first extension reaction product and the second extension reaction product in the presence of a first detector probe and a second detector probe to form an amplified first extension reaction product and an amplified second extension reaction product, wherein the first detector probe corresponds to the amplified first extension reaction product and the second detector probe corresponds to the second amplified second extension reaction product, wherein the stem of the first linker probe comprises a first sample identifying portion and the stem of the second linker probe comprises a second sample identifying portion, and the first detector probe hybridizes to the corresponding sample identifying portion of the amplified first extension reaction product and the second detector probe hybridizes to the corresponding sample identifying portion of the amplified second extension reaction product during the amplification reaction, wherein at least one of the first detector probe and the second detector probe further hybridizes to sequence corresponding to the small target polynucleotide during the amplification reaction; and, detecting the quantity of the small target polynucleotide in the two samples by comparing the first detector probe and the second detector probe.

2. The method according to claim 1 wherein the small target polynucleotide is a micro RNA.

3. The method according to claim 1 wherein at least one of the detector probes comprise peptide nucleic acid (PNA).

4. The method according to claim 1 wherein at least one of the detector probes is a 5'-nuclease cleavable probe.

5. The method according to claim 1 wherein each strand of the self-complementary stem of the first linker probe and/or second linker probe comprises 12-16 nucleotides.

6. The method according to claim 1 wherein the target specific portion of the first linker probe, the second linker probe, or both, comprises 6-8 nucleotides.

7. The method according to claim 1 wherein the loop further comprises a universal reverse primer portion.

8. The method according to claim 1 wherein the loop comprises 14-18 nucleotides.

9. The method according to claim 1,
wherein the first reaction mixture comprises a plurality of different linker probes corresponding to a plurality of different small target polynucleotide species,
wherein the second extension reaction mixture comprises a plurality of different linker probes corresponding to a plurality of different small target polynucleotide species,
wherein the pooled extension reaction products of the pooled reaction mixture are subsequently subdivided into a plurality of amplification reactions,
wherein each amplification reaction comprises a primer pair, a first detector probe corresponding to the first sample, and a second detector probe corresponding to the second sample,
wherein a small target polynucleotide is detected in each amplification reaction.

10. The method according to claim 9 wherein at least one primer pair comprises a forward primer corresponding to a small target polynucleotide, and a universal reverse primer corresponding to a universal reverse primer portion of a loop of the linker probe.

11. The method according to claim 1 wherein the detecting comprises an end-point analysis.

12. The method according to claim 1 wherein the detecting comprises a real-time analysis.

13. The method according to claim 12 wherein the real-time analysis is performed on a real-time thermal-cycler.

14. The method of claim 1, wherein the small target polynucleotide is 25 or fewer nucleotides in length.

* * * * *